US012715846B2

(12) United States Patent
Wang et al.

(10) Patent No.: US 12,715,846 B2
(45) Date of Patent: Aug. 25, 2026

(54) CRYSTAL FORM OF QUINOLINONE COMPOUND AND USE THEREOF

(71) Applicant: SUNSHINE LAKE PHARMA CO., LTD., Dongguan (CN)

(72) Inventors: Xiaojun Wang, Dongguan (CN); Liang Chen, Dongguan (CN); Yinglin Zuo, Dongguan (CN); Qiao Zong, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 1054 days.

(21) Appl. No.: 17/781,114

(22) PCT Filed: Nov. 26, 2020

(86) PCT No.: PCT/CN2020/131683

§ 371 (c)(1),
(2) Date: May 31, 2022

(87) PCT Pub. No.: WO2021/104353

PCT Pub. Date: Jun. 3, 2021

(65) Prior Publication Data

US 2023/0002325 A1 Jan. 5, 2023

(30) Foreign Application Priority Data

Nov. 28, 2019 (CN) ........................ 201911187714.7

(51) Int. Cl.

| | |
|---|---|
| ***C07D 215/56*** | (2006.01) |
| ***A61P 3/00*** | (2006.01) |
| ***A61P 7/06*** | (2006.01) |
| ***A61P 9/10*** | (2006.01) |
| ***A61P 17/02*** | (2006.01) |

(52) U.S. Cl.
CPC ........ *C07D 215/56* (2013.01); *C07B 2200/13* (2013.01)

(58) Field of Classification Search
CPC .................................................... C07D 215/56
See application file for complete search history.

(56) References Cited

U.S. PATENT DOCUMENTS 10,065,928 B2 9/2018 Zuo et al.

FOREIGN PATENT DOCUMENTS

| | | | |
|---|---|---|---|
| CN | 111269176 A | | 6/2020 |
| CN | 111269177 A | | 6/2020 |
| CN | 111269178 A | | 6/2020 |
| WO | WO 2016/034108 | * | 3/2016 |

OTHER PUBLICATIONS

Majmundar, “Hypoxia-Inducible Factors and the Response to Hypoxic Stress”, Molecular Cell, vol. 40, Issue 2, Oct. 22, 2010, pp. 294-309.*

Xie, “Association of endogenous erythropoietin with 10-year risk of all-cause and cardiovascular mortality”, Nutrition, Metabolism and Cardiovascular Diseases, 35 (2025), pp. 1-8.*

Mar. 3, 2021 International Search Report issued in Chinese Patent Application No. PCT/CN2020/131683.

Mar. 3, 2021 Wirtten Opinion of the International Searching Authority issued in Chinese Patent Application Mo. PCT/CN2020/131683.

* cited by examiner

*Primary Examiner* — Sahar Javanmard
(74) *Attorney, Agent, or Firm* — Oliff PLC

(57) ABSTRACT

A crystal form of a quinolinone compound and a use thereof further relating to a pharmaceutical composition including the crystal form, and a use of the crystal form or the pharmaceutical composition in the preparation of a drug for the treatment and prevention of HIF-related and/or EPO-related diseases (such as anemia).

10 Claims, 7 Drawing Sheets

CRYSTAL FORM OF QUINOLINONE COMPOUND AND USE THEREOF

CROSS-REFERENCE TO RELATED APPLICATION

This is a U.S. national stage application of the International Patent Application No. PCT/CN2020/131683, filed 26 Nov. 2020, which claims the priority of Chinese patent application with the application Ser. No. 201911187714.7 filed on Nov. 28, 2019, which is incorporated herein by reference in their entirety.

FIELD OF TECHNOLOGY

The invention belongs to the technical field of medicine, relates to a crystal form of quinolinone compound and use thereof, in particular relates to a crystal form of 2-(4-hydroxy-1-methyl-2-oxo-7-phenoxy-1,2-dihydroquinoline-3-carboxamido)acetic acid and use thereof, and further relates to a pharmaceutical composition comprising the crystal form.

BACKGROUND ART

In the case of anemia, trauma, tissue necrosis and defect, tissue or cells are often in a state of hypoxia. Hypoxia leads to the expression of a series of transcription-inducing factors involved in angiogenesis, iron, glucose metabolism, and cell growth and proliferation. Among them, hypoxia inducible factor (HIF) is a transcription factor initiated by somatic cells when oxygen is reduced, and is widely distributed in various parts of the body, especially in the intima of blood vessels, heart, brain, kidney, liver, etc. HIF is a heterodimer containing an oxygen-regulated α-subunit (HIF α) and a constitutively expressed β-subunit (HIF (3/ARNT). In oxygenated (normoxic) cells, the HIF α subunit is rapidly degraded by the mechanism of ubiquitination by the von Hippel-Lindau tumor suppressor (pVHL) E3 ligase complex. Under hypoxic conditions, HIF α is not degraded, and active HIF α/β complexes accumulate in the nucleus and activate the expression of various genes, including glycolytic enzymes, glucose transporters, erythropoietin (EPO) and vascular endothelial growth factor (VEGF).

Erythropoietin (EPO) is a naturally occurring hormone produced with HIF a, and it stimulates the production of red blood cells (erythrocytes) which carry oxygen throughout the body. EPO is normally secreted by the kidneys, and endogenous EPO increases under conditions of reduced oxygen (hypoxia). All types of anemia are characterized by a reduction in the blood's ability to carry oxygen and thus accompanied by similar signs and symptoms, including pale skin and mucous membranes, weakness, dizziness, easy fatigue, and lethargy, resulting in a reduced quality of life. Anemia is usually associated with a lack of red blood cells or hemoglobin in the blood. The common causes of anemia include the lack of iron, vitamin $B_{12}$, and folic acid, and can also be complicated by chronic diseases, such as inflammatory diseases, including the diseases with secondary myeloinflammatory suppression. Anemia is also associated with kidney dysfunction, and most patients with kidney failure on regular dialysis suffer from chronic anemia.

Prolyl hydroxylase domain (PHD) is a key factor in the regulation of HIF. Under normoxic conditions, PHD can hydroxylate the two key proline residues Pro402 and Pro564 of HIF a, and increase its affinity with pVHL and accelerate the degradation process. Under hypoxic and other pathological conditions, the HIF reaction catalyzed by PHD is blocked and the degradation rate of protease is slowed down, resulting in the accumulation of HIF a in cells, thereby causing a series of adaptive responses of cells to hypoxia. Inhibiting PHD by PHD inhibitors prolongs the effect of HIF, thereby increasing the expression of genes such as EPO, which can effectively treat and prevent HIF-related and/or EPO-related diseases, such as anemia, ischemia and hypoxia.

International application WO 2016034108 A1 discloses the compound 2-(4-hydroxy-1-methyl-2-oxo-7-phenoxy-1,2-dihydroquinoline-3-carboxamido)acetic acid (compound of formula (I)), which can treat or reduce HIF-related and/or EPO-related diseases, such as anemia. However, there is no research report on the crystal form of the compound in the prior art.

Error! Objects cannot be created from editing field codes. (I)

Drug polymorphism is a common phenomenon in drug development, and is an important factor affecting the quality of drugs. Different crystal forms of the same drug may have significant differences in appearance, solubility, melting point, dissolution, bioavailability, etc., and may have different effects on the stability, bioavailability and efficacy of the drug. Therefore, the drug should be fully considered the problem of polymorphism in drug research and development.

SUMMARY OF THE INVENTION

The present invention provides a crystal form of the compound of formula (I), wherein the crystal form, especially the crystal form I, can significantly improve the stability and pharmacokinetic properties of the compound, thereby having better druggability.

Specifically, the present invention relates to the crystal form of the compound of formula (I), and the use of the crystal form of the compound or the pharmaceutical composition in the manufacture of a medicament for treating or preventing HIF-related and/or EPO-related diseases. The crystal form provided herein can also be the form of solvate, such as hydrate.

In one aspect, provided herein is a crystal form of the compound of formula (I), (I)

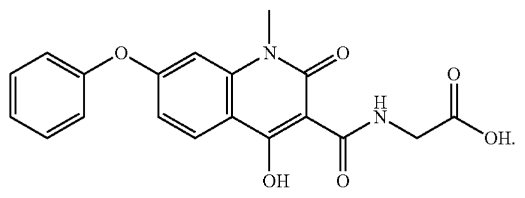

In some embodiments, the crystal form of the compound of formula (I) described herein is crystal form I or crystal form II.

In some embodiments, the crystal form I of the present invention is characterized in that the X-ray powder diffraction pattern of the crystal form I has diffraction peaks at the following 2θ angles: 6.20°±0.2°, 18.16°±0.2°, 19.30°±0.2°, 26.89°±0.2°, 27.31°±0.2°.

In other embodiments, the crystal form I of the present invention is characterized in that the X-ray powder diffraction pattern of the crystal form I has diffraction peaks at the following 2θ angles: 6.20°±0.2°, 9.05°±0.2°, 18.16°±0.2°, 19.30°±0.2°, 26.89°±0.2°, 27.31°±0.2°.

In other embodiments, the crystal form I of the present invention is characterized in that the X-ray powder diffraction pattern of the crystal form I has diffraction peaks at the following 2θ angles: 6.20°±0.2°, 9.05°±0.2°, 13.72°±0.2°, 18.16°±0.2°, 18.70°±0.2°, 19.30°±0.2°, 19.92°±0.2°, 22.06°±0.2°, 26.89°±0.2°, 27.31°±0.2°.

In some embodiments, the crystal form I of the present invention is characterized in that the X-ray powder diffraction pattern of the crystal form I has diffraction peaks at the following 2θ angles: 6.20°±0.2°, 7.32°±0.2°, 9.05°±0.2°, 13.72°±0.2°, 14.66°±0.2°, 15.18°±0.2°, 16.55°±0.2°, 18.16°±0.2°, 18.70°±0.2°, 19.30°±0.2°, 19.92°±0.2°, 20.28°±0.2°, 21.78°±0.2°, 22.06°±0.2°, 22.76°±0.2°, 23.39°±0.2°, 25.36°±0.2°, 25.68°±0.2°, 26.89°±0.2°, 27.31°±0.2°, 29.15°±0.2°, 29.49°±0.2°, 30.85°±0.2°, 31.39°±0.2°, 33.27°±0.2°, 34.36°±0.2°, 36.33°±0.2°, 37.15°±0.2°, 37.87°±0.2°, 38.43°±0.2°, 39.44°±0.2°, 40.71°±0.2°, 42.56°±0.2°, 42.94°±0.2°, 43.62°±0.2°, 44.25°±0.2°.

In some embodiments, the crystal form I of the present invention is characterized in that the X-ray powder diffraction pattern of the crystal form I has diffraction peaks at the following 2θ angles: 6.20°±0.2°, 7.32°±0.2°, 9.05°±0.2°, 13.72°±0.2°, 14.66°±0.2°, 15.18°±0.2°, 16.55°±0.2°, 18.16°±0.2°, 18.70°±0.2°, 19.30°±0.2°, 19.92°±0.2°, 20.28°±0.2°, 20.88°±0.2°, 21.78°±0.2°, 22.06°±0.2°, 22.76°±0.2°, 23.39°±0.2°, 25.36°±0.2°, 25.68°±0.2°, 26.89°±0.2°, 27.31°±0.2°, 29.15°±0.2°, 29.49°±0.2°, 30.85°±0.2°, 31.39°±0.2°, 33.27°±0.2°, 34.36°±0.2°, 36.33°±0.2°, 40.71°±0.2°, 42.56°±0.2°, 42.94°±0.2°, 43.62°±0.2°, 44.25°±0.2°.

In other embodiments, the crystal form I of the present invention is characterized in that the X-ray powder diffraction pattern of the crystal form I has diffraction peaks at the following 2θ angles: 6.20°±0.2°, 7.32°±0.2°, 9.05°±0.2°, 12.44°±0.2°, 13.72°±0.2°, 14.66°±0.2°, 15.18°±0.2°, 16.55°±0.2°, 18.16°±0.2°, 18.70°±0.2°, 19.30°±0.2°, 19.92°±0.2°, 20.28°±0.2°, 20.88°±0.2°, 21.78°±0.2°, 22.06°±0.2°, 22.76°±0.2°, 23.39°±0.2°, 25.36°±0.2°, 25.68°±0.2°, 26.89°±0.2°, 27.31°±0.2°, 29.15°±0.2°, 29.49°±0.2°, 30.85°±0.2°, 31.39°±0.2°, 33.27°±0.2°, 34.36°±0.2°, 36.33°±0.2°, 37.15°±0.2°, 37.87°±0.2°, 38.43°±0.2°, 39.44°±0.2°, 40.71°±0.2°, 42.56°±0.2°, 42.94°±0.2°, 43.62°±0.2°, 44.25°±0.2°, 45.46°±0.2°, 46.60°±0.2°, 48.43°±0.2°, 49.75°±0.2°, 52.66°±0.2°, 55.45°±0.2°, 56.36°±0.2°, 57.93°±0.2°.

In some embodiments, the crystal form I of the present invention is characterized in that the crystal form I has an X-ray powder diffraction pattern substantially as shown in FIG. 1.

In some embodiments, the crystal form I of the present invention is characterized in that the differential scanning calorimetry pattern of the crystal form I comprises an endothermic peak of 222.82° C.±3° C.

In some embodiments, the crystal form I of the present invention is characterized in that the crystal form I has a differential scanning calorimetry pattern substantially as shown in FIG. 2.

In some embodiments, the crystal form I of the present invention is characterized in that the crystal form I loses 1.315% in weight at about 70° C.-150° C., and the weight loss ratio has an error tolerance of ±0.1%.

In some embodiments, the crystal form II of the present invention is characterized in that the X-ray powder diffraction pattern of the crystal form II has diffraction peaks at the following 2θ angles: 5.23°, 13.61°, 25.90°, wherein the diffraction peak has an error tolerance of ±0.2°.

In some embodiments, the crystal form II of the present invention is characterized in that the X-ray powder diffraction pattern of the crystal form II has diffraction peaks at the following 2θ angles: 5.23°, 13.61°, 17.42°, 18.06°, 20.29°, 25.90°, 27.94°, wherein the diffraction peak has an error tolerance of ±0.2°.

In some embodiments, the crystal form II of the present invention is characterized in that the X-ray powder diffraction pattern of the crystal form II has diffraction peaks at the following 2θ angles: 5.23°, 8.73°, 10.12°, 10.52°, 13.61°, 15.80°, 17.42°, 18.06°, 19.99°, 20.29°, 20.93°, 21.54°, 22.72°, 24.08°, 25.18°, 25.90°, 27.94°, 30.04°, 32.19°, 33.13°, 35.21°, 35.99°, 36.95°, 40.09°, 41.17°, 45.55°, 48.48°, 51.97°, 55.75°, wherein the diffraction peak has an error tolerance of ±0.2°.

In some embodiments, the crystal form II of the present invention is characterized in that the crystal form II has an X-ray powder diffraction pattern substantially as shown in FIG. 4.

In some embodiments, the crystal form II of the present invention is characterized in that the differential scanning calorimetry pattern of the crystal form II comprises an endothermic peak of 223.69° C.±3° C.

In some embodiments, the crystal form II of the present invention is characterized in that the crystal form II has a differential scanning calorimetry pattern substantially as shown in FIG. 5.

In some embodiments, the crystal form II of the present invention is characterized in that the crystal form II loses 0.406% in weight at about 70° C.-160° C., and the weight loss ratio has an error tolerance of ±0.1%.

In another aspect, the present invention relates to a pharmaceutical composition comprising any one of the crystal forms described herein, and pharmaceutically acceptable carriers, excipients, diluents, adjuvants or combinations thereof.

In one aspect, the present invention relates to a use of any one of the crystal forms or the pharmaceutical composition in the manufacture of a medicament for preventing, treating or reducing hypoxia-inducible factor-related and/or erythropoietin-related diseases in a patient.

In some embodiments, the disease described herein is anemia, ischemia, vascular disease, angina pectoris, myocardial ischemia, myocardial infarction, metabolic disorder, or wound healing.

In another aspect, the present invention relates to a use of any one of the crystal forms or the pharmaceutical composition in the manufacture of a medicament for preventing, treating or reducing at least a part of diseases mediated by hypoxia-inducible factor prolyl hydroxylase in a patient.

In some embodiments, the disease described herein is anemia, ischemia, vascular disease, angina pectoris, myocardial ischemia, myocardial infarction, metabolic disorder, or wound healing.

One aspect of the present invention relates to a method of preventing, treating or reducing hypoxia-inducible factor-related and/or erythropoietin-related diseases in a patient, comprising administering a pharmaceutically acceptable effective dose of the crystal form or a pharmaceutically acceptable effective dose of the pharmaceutical composition of the present invention to a patient.

In another aspect, the present invention also relates to a method for preparing the crystal form of the compound of formula (I).

The solvent used in the method for preparing the crystal form of the invention is not particularly restricted, and any solvent which can dissolve the starting material to a degree and does not affect its properties is contained in the present invention. Additionally, many similar modifications in the art, equivalent replacements, or solvent, solvent combination and the solvent combination with different proportions which are equivalent to those described in the invention, are all deemed to be included in the present invention. The present invention gives the preferred solvent used in each reaction step.

The preparation of the crystal forms of the present invention will be described in detail in the examples section. Meanwhile, the present invention provides activity test experiments (e.g., pharmacokinetic experiments), solubility experiments, stability experiments, and hygroscopicity experiments of the crystal forms. Experiments have proved that the crystal form I of the present invention has better biological activity, solubility and stability than the crystal form II. In terms of stability, the crystal form II is unstable, and when it is left standing under normal temperature and pressure conditions, it is easy to undergo crystal transformation, transform into mixed crystals, and finally become a stable crystal form I; while the crystal form I described herein is very stable, does not undergo crystal transformation under normal conditions, and is also very stable under high temperature and high humidity conditions, with basically no change in appearance and purity. Therefore, the crystal form I of the present invention has better biological activity, better solubility and higher stability, and is suitable for pharmaceutical use.

In addition, according to the results of the hygroscopicity experiments, the crystal form I of the invention is not susceptible to high humidity and deliquescence, which is convenient for the long-term storage and placement of the medicine.

DEFINITIONS AND GENERAL TERMINOLOGY

Unless otherwise indicated, all technical and scientific terms used in the present invention have the same meaning as commonly understood by one of ordinary skill in the art to which this invention pertains. All patents and publications referred to herein are incorporated by reference in their entirety. Although any methods and materials similar or identical to those described herein may be used in the practice or testing of the invention, but the methods, apparatus and materials described in the invention are preferred.

"Crystal form" or "crystalline form" refers to a solid having a highly regular chemical structure, including, but not limited to, mono- or multi-component crystals, and/or polymorphic compounds of compounds, solvates, hydrates, clathrates, eutectics, salts, salt solvents, salt hydrates. The crystalline form of the material can be obtained by a number of methods known in the field. Such methods include, but are not limited to, melt crystallization, melt cooling, solvent crystallization, crystallization in defined space, for example, in nanopores or capillaries, crystallization on a surface or template, for example, on a polymer, crystallization in the presence of additives such as co-crystallization counterions, removing solvent, dehydration, rapid evaporation, rapid cooling, slow cooling, vapor diffusion, sublimation, reaction crystallization, anti-solvent addition, grinding and solvent drop milling, etc.

"Solvent" refers to a substance (typically a liquid) that is capable of completely or partially dissolving another substance (typically a solid). Solvents for use in the practice of this invention include, but are not limited to, water, acetic acid, acetone, acetonitrile, benzene, chloroform, carbon tetrachloride, dichloromethane, dimethylsulfoxide, 1,4-dioxane, ethanol, ethyl acetate, butanol, t-butanol, N,N-dimethylacetamide, N,N-dimethylformamide, formamide, formic acid, heptane, hexane, isopropanol, methanol, methyl ethyl ketone, mesitylene, nitromethane, polyethylene glycol, propanol, pyridine, tetrahydrofuran, toluene, xylene, mixtures thereof, and the like.

"Anti-solvent" refers to a fluid that promotes the precipitation of a product (or product precursor) from a solvent. The anti-solvent may comprise a cold gas, or a fluid that promotes the precipitation of the fluid by chemical reaction or reduces the solubility of the product in the solvent; it may be the same liquid as the solvent but at a different temperature, or it may be a liquid different from the solvent.

"Solvate" refers to a compound that on a surface, in a lattice or having a solvent on a surface or in a lattice. The solvent can be water, acetic acid, acetone, acetonitrile, benzene, chloroform, carbon tetrachloride, dichloromethane, dimethylsulfoxide, 1,4-dioxane, ethanol, ethyl acetate, butanol, t-butanol, N,N-dimethylacetamide, N,N-dimethylformamide, formamide, formic acid, heptane, hexane, isopropanol, methanol, methyl ethyl ketone, methyl pyrrolidone, mesitylene, nitromethane, polyethylene glycol, propanol, pyridine, tetrahydrofuran, toluene, xylene, mixtures thereof, and the like. A specific example of the solvate is a hydrate in which the solvent on the surface, in the lattice or both on the surface and in the lattice is water. On the surface, in the lattice or both on the surface and in the lattice of the substance, the hydrate may or may not have any solvent other than water.

Crystal form can be identified by a variety of technical means, such as X-ray powder diffraction (XRPD), infrared absorption spectroscopy (IR), melting point method, differential scanning calorimetry (DSC), thermogravimetric analysis (TGA), Nuclear magnetic resonance, Raman spectroscopy, X-ray single crystal diffraction, dissolution calorimetry, scanning electron microscopy (SEM), quantitative analysis, solubility and dissolution rate, etc.

X-ray powder diffraction (XRPD) can detect changes in crystal form, crystallinity, crystal state and other information. It is a common mean for identifying crystal form. The peak position of the XRPD pattern primarily depends on the structure of the crystal form and is relatively insensitive to the experimental details, and its relative peak height depends on many factors associated with sample preparation and instrument geometry. Thus, in some embodiments, the crystalline form of the present invention is characterized by an XRPD pattern having certain peak positions, which is substantially as shown in the XRPD pattern provided in the drawings of the present invention. At the same time, the measurement of 2θ of the XRPD pattern can have experimental errors, the measurement of 2θ of the XRPD pattern may be slightly different between the different instruments and the different samples. Therefore, the values of 2θ cannot be regarded as absolute. According to the condition of the instrument used in this test, the diffraction peak has an error tolerance of ±0.2°.

Differential Scanning Calorimetry (DSC) is a technique of measuring the energy difference between a sample and an inert reference (commonly used $\alpha$-$Al_2O_3$) with temperature by continuously heating or cooling under program control. The endothermic peak height of the DSC curve depends on many factors associated with sample preparation and instrument geometry, while the peak position is relatively insensitive to experimental details. Thus, in some embodiments, the crystal form of the present invention is characterized by an DCS pattern having certain peak positions, which is substantially as shown in the DCS pattern provided in the drawings of the present invention. At the same time, the DCS pattern can have experimental errors, the peak positions and peak values of DCS pattern may be slightly different between the different instruments and the different samples. Therefore, the peak positions or the peak values of the DSC endothermic peak cannot be regarded as absolute. According to the condition of the instrument used in this test, the endothermic peak has an error tolerance of ±3°.

Thermogravimetric analysis (TGA) is a technique for measuring the quality of a substance with temperature under the control of a program. It is suitable for examining the process of the solvent loss or the samples sublimation and decomposition. It can be presumed that the crystal contains crystal water or crystallization solvent. The quality variety of the TGA curve shown depend on a number of factors, containing the sample preparation and the instrument. The quality variety of the TGA test may be slightly different between the different instruments and between the different samples. According to the condition of the instrument used in this test, there is a ±0.1% error tolerance for the mass change.

In the context of the present invention, the 2θ values in the X-ray powder diffraction pattern are in degrees (°).

The term "substantially as shown in the figure" refers to at least 50%, or at least 60%, or at least 70%, or at least 80%, or at least 90%, or at least 95%, or at least 99% of the peaks are shown in the X-ray powder diffraction pattern or DSC pattern or Raman spectra pattern or infrared spectra pattern.

The "peak" refers to a feature that a person skilled in the art can recognize without belonging to background noise when referring to a spectrum or/and data that appears in the figure.

The present invention relates to a novel crystal form of 2-(4-hydroxy-1-methyl-2-oxo-7-phenoxy-1,2-dihydroquinoline-3-carboxamido)acetic acid, such as crystal form I or II, which exist in substantially pure crystal form.

"Substantially pure" means that a crystalline form is substantially free of another or more crystalline forms, that means the purity of the crystalline form is at least 80%, or at least 85%, or at least 90%, or at least 93%, or at least 95%, or at least 98%, or at least 99%, or at least 99.5%, or at least 99.6%, or at least 99.7%, or at least 99.8%, or at least 99.9%, or crystal form containing other crystal form. The percentage of the other crystal form in the total volume or total weight of the crystal form is less than 20%, or less than 10%, or less than 5%, or less than 3%, or less than 1%, or less than 0.5%, or less than 0.1%, or less than 0.01%.

"Substantially free" means that the percentage of one or more other crystalline forms in the total volume or total weight of the crystalline form is less than 20%, or less than 10%, or less than 5%, or less than 4% , or less than 3%, or less than 2%, or less than 1%, or less than 0.5%, or less than 0.1%, or less than 0.01%.

"Relative strength" (or "relative peak height") in the XRPD pattern means the ratio of the intensity of the other peaks to the intensity of the first strong peak when the intensity of the first strong peak in all the diffraction peaks of the X-ray powder diffraction pattern (XRD) is 100%.

In the context of the present invention, when or whether the words, such as "about" or "approximately", are used, it means within 10%, appropriately within 5%, especially within 1% of the given value or range. Alternatively, for those of ordinary skill in the art, the term "about" or "approximately" means within an acceptable standard error range of the mean value. Whenever a number with a value of N is disclosed, any number within N+/−1%, N+/−2%, N+/−3%, N+/−5%, N+/−7%, N+/−8%, or N+/−10% of the value will be explicitly disclosed, wherein "+/−" means plus or minus.

In the present invention, "room temperature" refers to the temperature from about 10° C. to about 40° C. In some embodiments, "room temperature" refers to a temperature from about 20° C. to about 30° C.; in other embodiments, "room temperature" refers to 20° C., 22.5° C., 25° C., 27.5° C., etc.

Compositions, Formulations, Administration and Uses of the Crystal Forms of the Present Invention The characteristics of the pharmaceutical composition of the present invention include the crystal form of the compound of formula (I) and pharmaceutically acceptable carriers, adjuvants, or excipients. The amount of the compound crystal form in the pharmaceutical composition of the present invention can effectively and detectably treat or reduce HIF-related and/or EPO-related diseases in a patient.

As described herein, the pharmaceutically acceptable compositions disclosed herein further comprise pharmaceutically acceptable carriers, adjuvants, or excipients, which, as used herein, include any solvents, diluents, or other liquid vehicle, dispersion or suspension agents, surface active agents, isotonic agents, thickening or emulsifying agents, preservatives, solid binders, lubricants and the like, as suited to the particular dosage form desired. As described in the following: In Remington: The Science and Practice of Pharmacy, 21st edition, 2005, ed. D.B. Troy, Lippincott Williams& Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the crystal forms of the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The pharmaceutical compositions disclosed herein can be capsules, tablets, pills, powders, granules and aqueous suspensions or solutions; and may be administered orally, parenterally, by inhalation spray, topically, rectally, nasally, buccally, vaginally or via an implanted reservoir.

Oral administration can be administered in the following forms: tablets, pills, capsules, dispersible powders, granules or suspensions, syrups, elixirs, etc.; topical administration can be administered in the following forms: ointments, gels, medicated tape, etc.

The crystal forms of the present invention are preferably formulated in dosage form according to the formulation to reduce the dose and dose uniformity. The term "dosage unit type" herein refers to a physically dispersed unit in which a patient obtains the appropriate treatment. However, it should be understood that the daily general use of the compound of formula (I) or its crystal form, or the pharmaceutical composition of the present invention will be determined by the attending physician on the basis of a reliable medical range judgment. The specific effective dose level for any particular patient or organism will depend on a number of factors including the severity of the disease and condition being treated, the activity of the particular compound or its crystal form, the particular composition used, the age, weight, health, sex and eating habits of the patient, time of administration, route of administration and excretion rate of the particular compound or its crystal form used, duration of treatment, drug use in combination or in combination with a specific compound or its crystal form, and other well known factors in the field of pharmacy.

The effective dose of active ingredient used may vary with the compound or its crystal form, the mode of administration, and the severity of the disease to be treated. Generally, however, satisfactory results are obtained when the compound of the present invention or its crystal form is administered in a daily dose of about 0.25-1000 mg/kg of animal body weight, preferably in 2-4 divided doses per day, or in sustained release form. This dosage regimen can be adjusted to provide optimal therapeutic response. In addition, several divided doses may be administered daily or the dose may be proportionally reduced depending upon the condition being treated.

The compound or its crystal form, and the pharmaceutical composition of the present invention can be used to inhibit HIF hydroxylase activity, thereby regulating the stability and/or activity of HIF and activating the expression of HIF-regulated genes. The compound or its crystal form or the pharmaceutical composition can be used in a method of treating, pre-treating or delaying the onset or progression of HIF-related diseases, such diseases include, but are not limited to, anemia and various aspects of ischemia and hypoxia.

Specifically, the compound involved in the present invention or its crystal form can be used to increase endogenous erythropoietin (EPO). The compound or its crystal form can be administered to prevent, pre-treat, or treat EPO-related diseases, including, for example, anemia and neurological diseases. Diseases associated with anemia include, but are not limited to, acute or chronic kidney disease, diabetes, cancer, ulcers, viral (e.g., HIV), bacterial or parasitic infections; inflammation, etc. Anemia diseases can further be associated with procedures or treatments including, for example, radiation therapy, chemotherapy, dialysis, and surgery. In addition, anemia is associated with abnormalities in hemoglobin and/or red blood cells, as seen in diseases such as microcytic anemia, hypochromic anemia, aplastic anemia, and the like.

EMBODIMENTS

Figure 1:
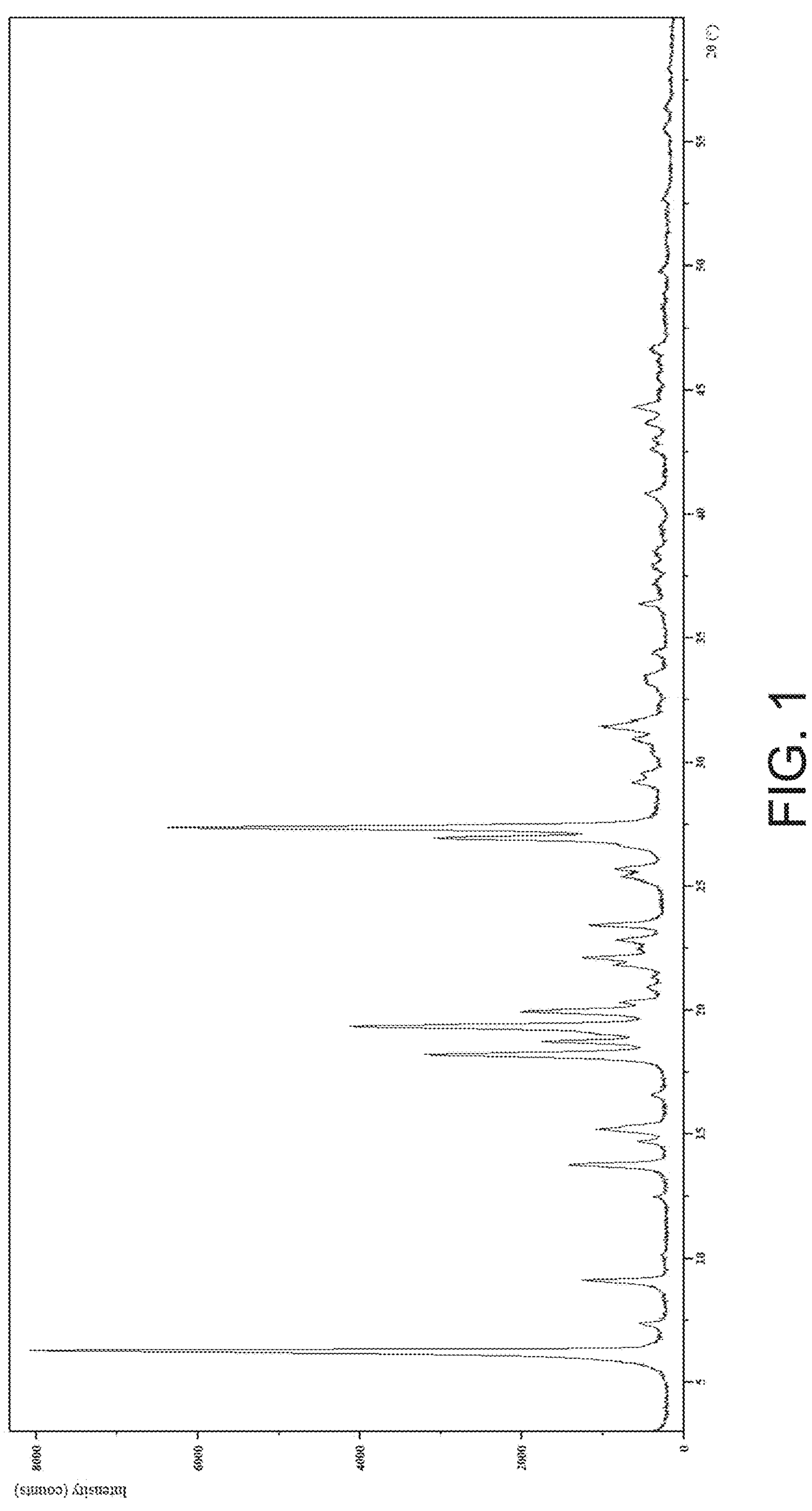
FIG. 1 is an X-ray powder diffraction (XRPD) pattern of the crystal form I of the compound of formula (I).

The invention will now be further described by way of example without limiting the invention to the scope of the invention.

The X-ray powder diffraction analysis method used in the present invention was an Empyrean diffractometer, and an X-ray powder diffraction pattern was obtained using Cu-Kα radiation (45 KV, 40 mA). The powdery sample was prepared as a thin layer on a monocrystalline silicon sample rack and placed on a rotating sample stage, analyzed at a rate of 0.0167° steps in the range of 3°-60°. Data Collector software was used to collect data, HighScore Plus software was used to process data, and Data Viewer software was used to read data.

The differential scanning calorimetry (DSC) analysis method used in the present invention is a differential scanning calorimeter using a TA Q2000 module with a thermal analysis controller. Data were collected and analyzed using TA Instruments Thermal Solutions software. Approximately 1-5 mg of the sample was accurately weighed into a specially crafted aluminum crucible with a lid and analyzed from room temperature to about 300° C. using a linear heating device at 10° C./min. During use, the DSC chamber was purged with dry nitrogen.

The thermogravimetric analysis (TGA) method used herein was that thermogravimetric loss was performed using a TA Q500 module with a thermal analysis controller. Data were collected and analyzed using TA Instruments Thermal Solutions software. Approximately 10 mg of the sample was accurately weighed into a platinum sample pan and analyzed from room temperature to about 300° C. using a linear heating device at 10° C./min. During use, the TGA chamber was purged with dry nitrogen.

The solubility of the present invention was determined using an Agilent 1200 High Performance Liquid Chromatograph DAD/VWD detector with an Agilent XDB-C18 model (4.6×50 mm, 5 μm). The detection wavelength was 266 nm, the flow rate was 1.0 mL/min, and the column temperature was 35° C. The mobile phase A was acetonitrile–0.01 M ammonium acetate=10:90 (V:V), and the analysis method was acetonitrile–mobile phase A=70:30 (V:V). The running time was 10 minutes.

The hygroscopicity of the present invention was measured by a DVS INT-Std dynamic moisture and gas adsorption analyzer from Surface Measurement Systems, UK. The humidity test range was 0%-95%, the airflow rate was 200 mL/min, and the temperature was 25° C. One test point was taken for every 5% increase in humidity.

Embodiment Methods

The specific synthesis method of compound 2-(4-hydroxy-1-methyl-2-oxo-7-phenoxy-1,2-dihydroquinoline-3-carboxamido)acetic acid of formula (I) refers to Example 1 in International Application WO 2016034108 A1.

EXAMPLES

Example 1

Crystal Form I of the Present Invention

1. Preparation of Crystal Form I

Method One:

To 2-(4-hydroxy-1-methyl-2-oxo-7-phenoxy-1,2-dihydroquinoline-3-carboxamido)acetic acid (40.0 mg) prepared according to the method of prior art was added 1,4-dioxane (1.5 mL), after the solid was completely dissolved, water (1.5 mL) was added dropwise. After the crystals were precipitated, the mixture was suction filtered, and the filter cake was dried in vacuum at room temperature to obtain an off-white solid (38.8 mg, 97.0%).

Method Two:

To 2-(4-hydroxy-1-methyl-2-oxo-7-phenoxy-1,2-dihydroquinoline-3-carboxamido)acetic acid (26.3 mg) prepared according to the method of prior art was added methanol (6.0 mL), the mixture was heated to 60° C. to completely dissolve the solid, the temperature was kept for 30 minutes, then quenched to −10° C. After the crystals were precipitated, the mixture was suction filtered, and the filter cake was dried in vacuum at room temperature to obtain an off-white solid (12.2 mg, 46.4%).

2. Identification of Crystal Form I (1) Analysis and identification by Empyrean X-ray powder diffraction (XRPD) using Cu-Kα radiation: the X-ray powder diffraction pattern has the following characteristic peaks at 2θ angles: 6.20°, 7.32°, 9.05°, 12.44°, 13.72°, 14.66°, 15.18°, 16.55°, 18.16°, 18.70°, 19.30°, 19.92°, 20.28°, 20.88°, 21.78°, 22.06°, 22.76°, 23.39°, 25.36°, 25.68°, 26.89°, 27.31°, 29.15°, 29.49°, 30.85°, 31.39°, 33.27°, 34.36°, 36.33°, 37.15°, 37.87°, 38.43°, 39.44°, 40.71°, 42.56°, 42.94°, 43.62°, 44.25°, 45.46°, 46.60°, 48.43°, 49.75°, 52.66°, 55.45°, 56.36° and 57.93°. There is an error tolerance of ±0.2°.

(2) Analysis and identification by TA Q2000 Differential Scanning Calorimetry (DSC): the scanning speed was 10° C./min, and the pattern contained an endothermic peak of 222.82° C. There is an error tolerance of ±3° C.

(3) Analysis and identification of thermogravimetric (TGA) by TA Q500: the heating rate was 10° C./min, and the weight loss range was 1.315%. There is an error tolerance of ±0.1%.

Example 2

Crystal Form II of the Present Invention

1. Preparation of Crystal Form II

Method One:

2-(4-Hydroxy-1-methyl-2-oxo-7-phenoxy-1,2-dihydroquinoline-3-carboxamido)acetic acid (50.7 mg) prepared according to the method of prior art was dissolved in dimethylformamide (2.0 mL), then water (1.5 mL) was added dropwise. After the crystals were precipitated, the mixture was suction filtered, and the filter cake was dried in vacuum at room temperature to obtain an off-white solid (39.7 mg, 78.3%).

Method Two:

To 2-(4-hydroxy-1-methyl-2-oxo-7-phenoxy-1,2-dihydroquinoline-3-carboxamido)acetic acid (75.1 mg) prepared according to the method of prior art was added dimethylformamide (1.0 mL) to dissolve, then water (5.0 mL) was added dropwise to the reaction solution. After the crystals were precipitated, the mixture was suction filtered, and the filter cake was dried in vacuum at room temperature to obtain an off-white solid (64.5 mg, 85.9%).

2. Identification of Crystal Form II (1) Analysis and identification by Empyrean X-ray powder diffraction (XRPD) using Cu-Kα radiation: the X-ray powder diffraction pattern has the following characteristic peaks at 2θ angles : 5.23°, 8.73°, 10.12°, 10.52°, 13.61°, 15.80°, 17.42°, 18.06°, 19.99°, 20.29°, 20.93°, 21.54°, 22.72°, 24.08°, 25.18°, 25.90°, 27.94°, 30.04°, 32.19°, 33.13°, 35.21°, 35.99°, 36.95°, 40.09°, 41.17°, 45.55°, 48.48°, 51.97° and 55.75°. There is an error tolerance of ±0.2°.

(2) Analysis and identification by TA Q2000 Differential Scanning Calorimetry (DSC): the scanning speed was 10° C./min, and the pattern contained an endothermic peak of 223.69° C. There is an error tolerance of ±3° C.

(3) Analysis and identification of thermogravimetric (TGA) by TA Q500: the heating rate was 10° C./min, and the weight loss range was 0.406%. There is an error tolerance of ±0.1%.

Example 3

Pharmacokinetic Experiment of the Crystal Form of the Present Invention

The crystal form of the compound of formula (I) of the present invention is filled into capsules for oral administration.

8-12 kg male Beagle dogs were taken, and 3 as a group. Capsules containing the test sample were orally administered at a dose of 10 mg/kg and the bloods were collected at time points of 0.25, 0.5, 1.0, 2.0, 4.0, 6.0, 8.0 and 24 h. Standard curve was plotted based on concentrations of the samples in a suitable range, the concentration of the test sample in the plasma sample was measured and quantified by AB SCIEX API4000 LC-MS/MS at MRM mode. Pharmacokinetic parameters were calculated according to drug concentration-time curve using a noncompartmental method by WinNonLin 6.3 software. Results are as shown in table 1.

TABLE 1

Pharmacokinetic experimental data of the crystal form of the present invention

| Test sample | $T_{max}$ (h) | $C_{max}$ (ng/ml) | $AUC_{last}$ (h*ng/ml) |
|---|---|---|---|
| Example 1 (crystal form I) | 1.17 | 2810 | 9300 |

Conclusion:

It can be seen from Table 1 that the crystal form I of the present invention has a larger exposure in beagle dogs and has better pharmacokinetic properties.

Example 4

The Stability Experiment of the Crystal Form of the Present Invention (1) High-temperature experiment: appropriate amount of the test sample was added into a flat weighing bottle, divided into ≤5 mm thick thin layer. The bottle was placed at 60° C.±2° C. for 30 days. Samples were taken on the 6th, 10th, and 30th day, and tested according to the key stability inspection items: the color of the samples were observed, the purities of the samples were determined by HPLC. The experimental results are shown in Table 2.

(2) High-humidity experiment: a batch of the test sample was added into a flat weighing bottle, divided into ≤5 mm thick thin layer. The bottle was placed at 25° C. and RH for 90%±5% for 30 days. Samples were taken on the 6th, 10th, and 30th day, and tested according to the key stability inspection items: the color of the samples were observed, the purities of the samples were determined by HPLC. The experimental results are shown in Table 2.

(3) Illumination experiment: a batch of the test sample was added into a flat weighing bottle, divided into ≤5mm thick thin layer. The bottle was opened and placed in a light box (with UV lamp) under the condition of illuminance of 4500±500 lx and ultraviolet light ≥0.7w/$m^2$ for 30 days. Samples were taken on the 6th, 13th, and 30th day, the purities of the samples were determined by HPLC. The experimental results are shown in Table 2.

(4) Accelerated experiment: appropriate amount of the test sample was packed with a single-layer PE and aluminum foil, the sample was placed at 40±2° C./75%±5% RH for 6 months. Samples were taken on the 1st, 2nd, 3rd and 6th month. The color of the samples were observed, the purities of the samples were determined by HPLC, and the moisture content was determined by TGA. The experimental results are shown in Table 3.

TABLE 2

Results of high-temperature, high-humidity and illumination experiments of crystal form I of the present invention

| | | Condition | | | | | | | | |
|---|---|---|---|---|---|---|---|---|---|---|
| | | High temperature (60° C.) | | | High humidity (RH92.5%) | | | Illumination | | |
| Item | 0 day | 6th day | 10th day | 30th day | 6th day | 10th day | 30th day | 6th day | 13th day | 30th day |
| Appearance | off-white solid | off-white solid | off-white solid | off-white solid | off-white solid | off-white solid | off-white solid | off-white solid | off-white solid | off-white solid |
| Purity/% | 99.76 | 99.77 | 99.78 | 99.77 | 99.78 | 99.77 | 99.76 | 99.77 | 99.77 | 99.72 |

TABLE 3

[]Results of the accelerated-experiment (40 ± 2° C./75% ± 5% RH) of the crystal form I of the present invention

| Item | 0 month | 1st month | 2nd month | 3rd month | 6th month |
|---|---|---|---|---|---|
| Appearance | off-white solid | off-white solid | off-white solid | off-white solid | off-white solid |

TABLE 3-continued

[]Results of the accelerated-experiment (40 ± 2° C./75% ± 5% RH) of the crystal form I of the present invention

| Item | 0 month | 1st month | 2nd month | 3rd month | 6th month |
|---|---|---|---|---|---|
| Moisture content/% | 0.04 | 0.06 | 0.07 | 0.08 | 0.12 |
| Purity/% | 99.78 | 99.77 | 99.78 | 99.78 | 99.78 |

Conclusion:

It can be seen from the results in Table 2, under high temperature (60° C.), high humidity (25° C., RH 90%±5%), and lighting conditions for 30 days, the appearance and purity of the crystal form I of the present invention have no obvious changes.

It can be seen from the results in Table 3, under the accelerated experimental conditions, the appearance, purity and moisture content of the crystal form I of the present invention have no obvious changes.

To sum up, the crystal form I of the present invention has good stability under various setting conditions, and is suitable for pharmaceutical use.

Example 5

Hygroscopicity Experiment of the Crystal Form of the Present Invention

An appropriate amount of the test sample was taken, the hygroscopicity was tested by dynamic moisture adsorption device.

Figure 7:
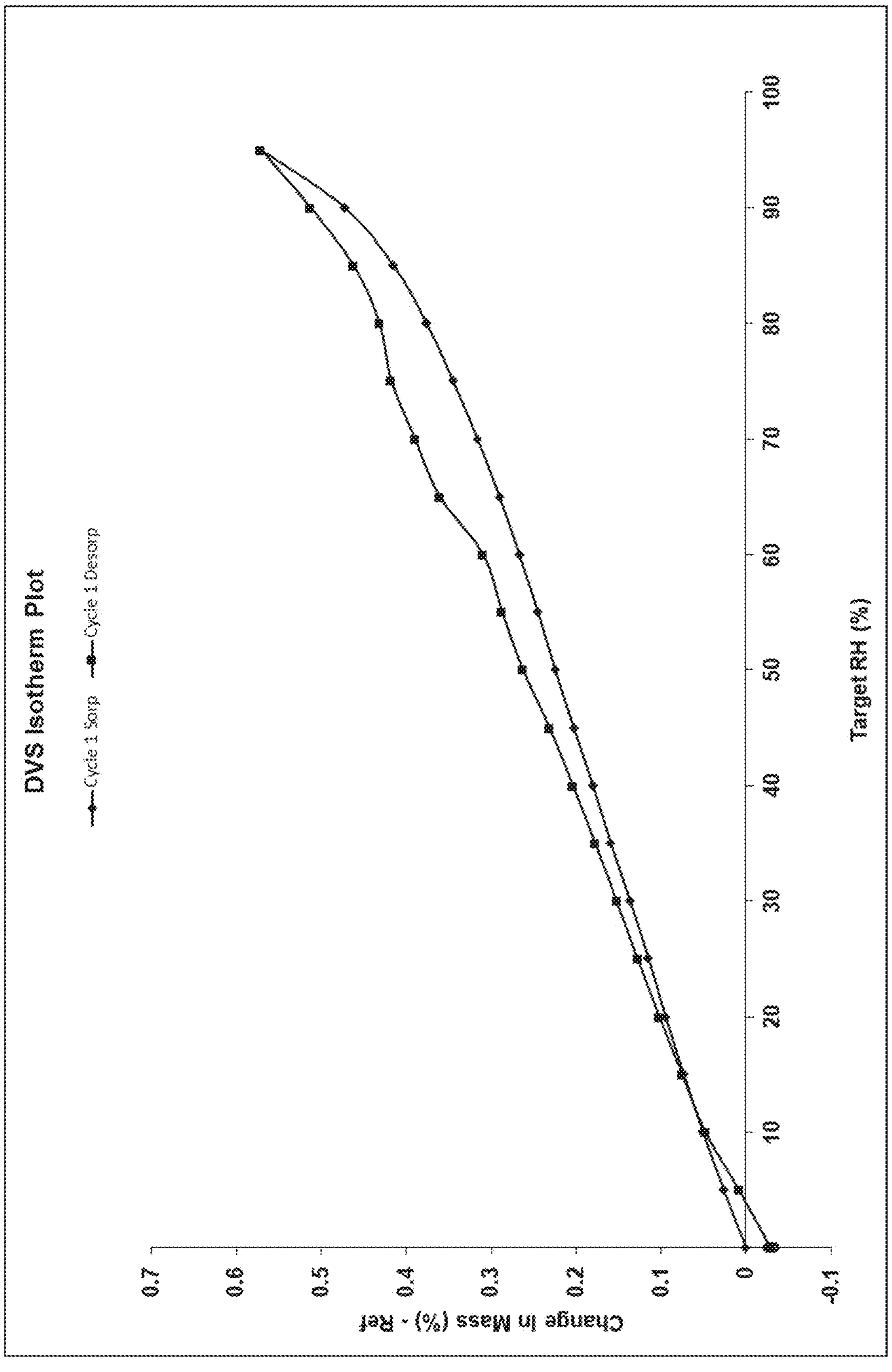
FIG. 7 is a dynamic moisture adsorption (DVS) pattern of the crystal form I of the compound of formula (I).

Wherein, the DVS pattern of the hygroscopicity test of the crystal form I of the present invention is basically as shown in FIG. 7, and the specific experimental results are shown in Table 4. According to the description of the hygroscopicity feature and the definition of the hygroscopicity gain (General Principle 9103 of Chinese Pharmacopoeia 2015 Edition, the guiding principle of drug hygroscopicity test, see Table 5 for details), the crystal form I of the present invention is lightly hygroscopic and is not easily affected by high humidity and deliquescence.

TABLE 4

| ]The hygroscopicity experiment of the crystal form I of the present invention | | | |
|---|---|---|---|
| Test sample | Weight gain at 60% relative humidity/% | Weight gain at 80% relative humidity/% | Weight gain at 95% relative humidity/% |
| Crystal form I | 0.27 | 0.38 | 0.57 |

TABLE 5

| []Description of the hygroscopicity feature and the definition of the hygroscopicity weight gain (25° C. ± 1° C., 80% ± 2% relative humidity) | |
|---|---|
| the hygroscopicity feature | the hygroscopicity weight gain |
| deliquescence | absorb enough water to form a liquid |
| highly hygroscopicity | not less than 15% |
| hygroscopicity | less than 15% but not less than 0.2% |
| lightly hygroscopicity | less than 2% but not less than 0.2% |
| No or almost none hygroscopicity | less than 0.2% |

The foregoing description is merely a basic illustration of the present invention and any equivalent transformation made in accordance with the technical solution of the present invention is intended to be within the scope of the present invention.

Reference throughout this specification to "an embodiment," "some embodiments," "one embodiment", "a specific example," or "some examples," means that a particular feature, structure, material, or characteristic described in connection with the embodiment or example is included in at least one embodiment or example of the present disclosure. The appearances of the phrases in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments within the scope of the present disclosure.

What is claimed is:

1. The crystal form I of the compound of formula (I), wherein the X-ray powder diffraction pattern of the crystal form I has diffraction peaks at the following 2θ angles: 6.20°±0.2°, 18.16°±0.2°, 19.30°±0.2°, 26.89°±0.2°, 27.31°±0.2°;

(I)

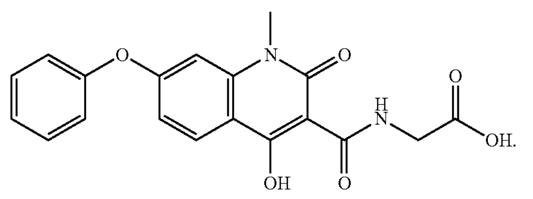

2. The crystal form I of claim 1, wherein the X-ray powder diffraction pattern of the crystal form I has diffraction peaks at the following 2θ angles: 6.20°±0.2°, 9.05°±0.2°, 13.72°±0.2°, 18.16°±0.2°, 18.70°±0.2°, 19.30°±0.2°, 19.92°±0.2°, 22.06°±0.2°, 26.89°±0.2°, 27.31°±0.2°.

3. The crystal form I of claim 1, wherein the X-ray powder diffraction pattern of the crystal form I has diffraction peaks at the following 2θ angles: 6.20°±0.2°, 7.32°±0.2°, 9.05°±0.2°, 13.72°±0.2°, 14.66°±0.2°, 15.18°±0.2°, 16.55°±0.2°, 18.16°±0.2°, 18.70°±0.2°, 19.30°±0.2°, 19.92°±0.2°, 20.28°±0.2°, 21.78°±0.2°, 22.06°±0.2°, 22.76°±0.2°, 23.39°±0.2°, 25.36°±0.2°, 25.68°±0.2°, 26.89°±0.2°, 27.31°±0.2°, 29.15°±0.2°, 29.49°±0.2°, 30.85°±0.2°, 31.39°±0.2°, 33.27°±0.2°, 34.36°±0.2°, 36.33°±0.2°, 37.15°±0.2°, 37.87°±0.2°, 38.43°±0.2°, 39.44°±0.2°, 40.71°±0.2°, 42.56°±0.2°, 42.94°±0.2°, 43.62°±0.2°, 44.25°±0.2°.

4. The crystal form I of claim 1, wherein the X-ray powder diffraction pattern of the crystal form I has diffraction peaks at the following 2θ angles: 6.20°±0.2°, 7.32°±0.2°, 9.05°±0.2°, 12.44°±0.2°, 13.72°±0.2°, 14.66°±0.2°, 15.18°±0.2°, 16.55°±0.2°, 18.16°±0.2°, 18.70°±0.2°, 19.30°±0.2°, 19.92°±0.2°, 20.28°±0.2°, 20.88°±0.2°, 21.78°=0.2°, 22.06°±0.2°, 22.76°±0.2°, 23.39° ±0.2°, 25.36°±0.2°, 25.68°±0.2°, 26.89°±0.2°, 27.31°±0.2°, 29.15°±0.2°, 29.49°±0.2°, 30.85°±0.2°, 31.39°±0.2°, 33.27°±0.2°, 34.36°±0.2°, 36.33°±0.2°, 37.15°'0.2°, 37.87°±0.2°, 38.43°±0.2°, 39.44°±0.2°, 40.71°±0.2°, 42.56°±0.2°, 42.94°±0.2°, 43.62°±0.2°, 44.25°±0.2°, 45.46°±0.2°, 46.60°±0.2°, 48.43°±0.2°, 49.75°±0.2°, 52.66°±0.2°, 55.45°±0.2°, 56.36°±0.2°, 57.93°±0.2°.

5. The crystal form I of claim 1, wherein the crystal form I has an X-ray powder diffraction pattern substantially as shown in FIG. 1.

6. The crystal form I of claim 1, wherein the differential scanning calorimetry pattern of the crystal form I comprises an endothermic peak of 222.82° C. ±3° C.

Figure 2:
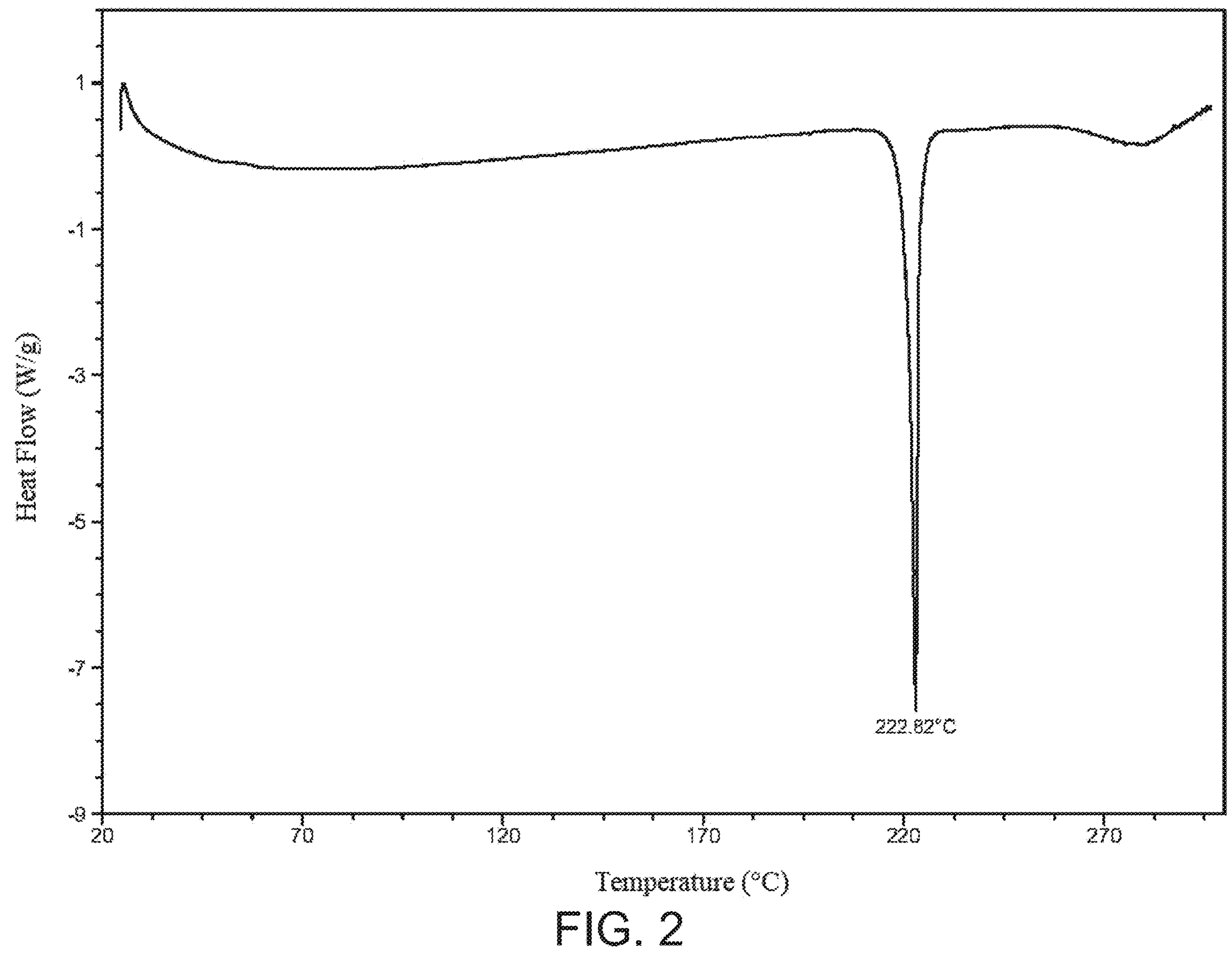
FIG. 2 is a differential scanning calorimetry (DSC) pattern of the crystal form I of the compound of formula (I).
Figure 3:
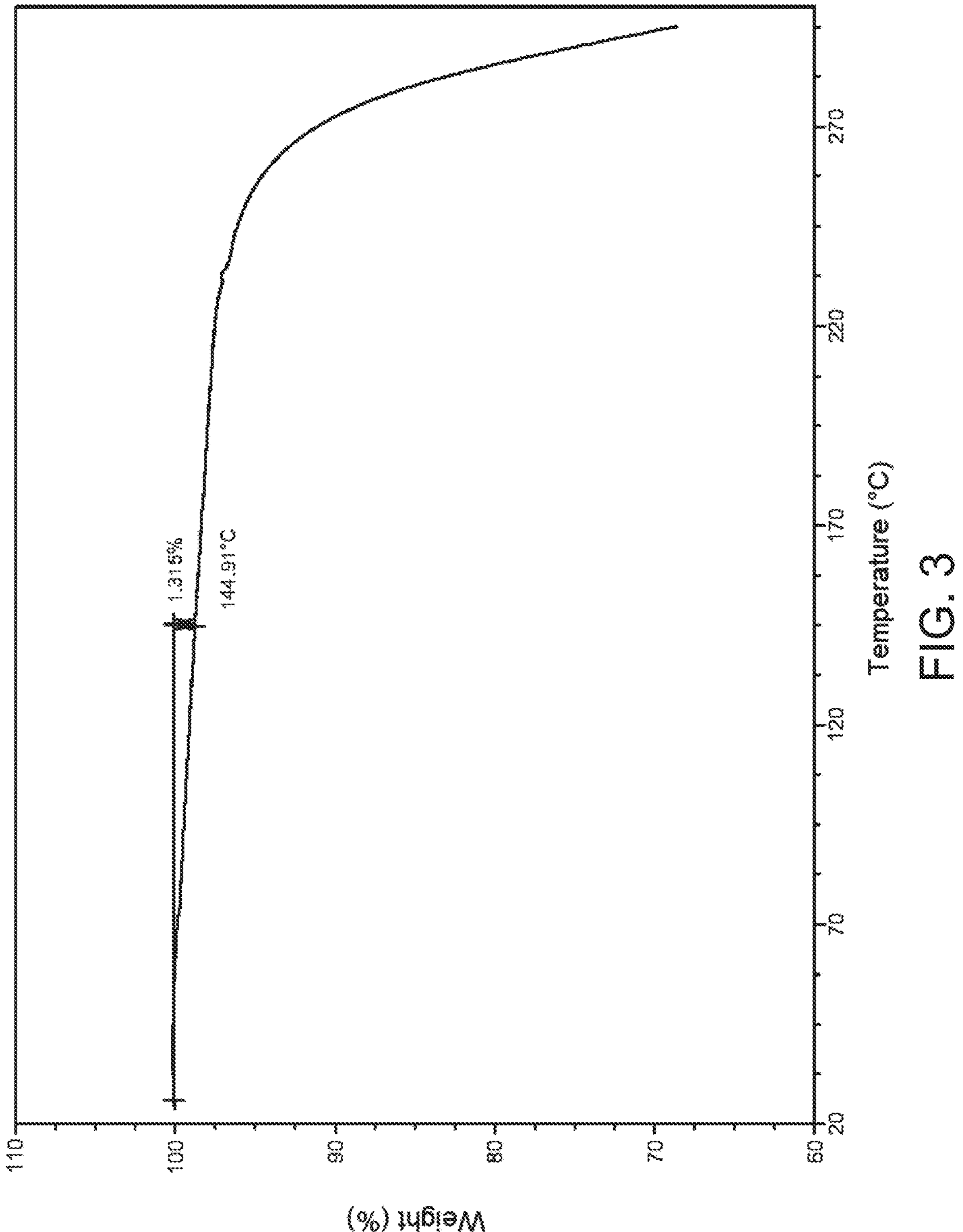
FIG. 3 is a thermogravimetric analysis (TGA) pattern of the crystal form I of the compound of formula (I).
Figure 4:
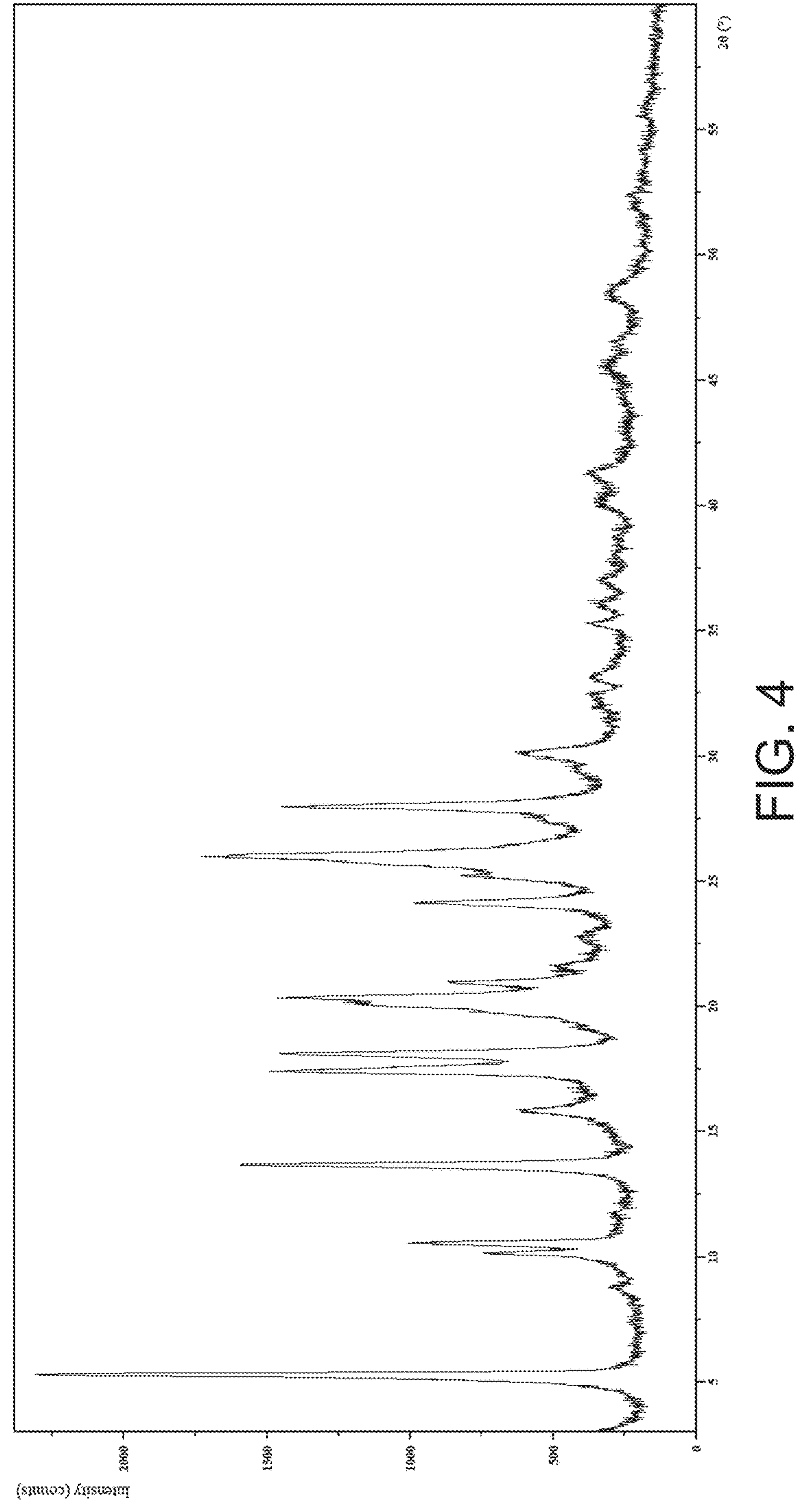
FIG. 4 is an X-ray powder diffraction (XRPD) pattern of the crystal form II of the compound of formula (I).
Figure 5:
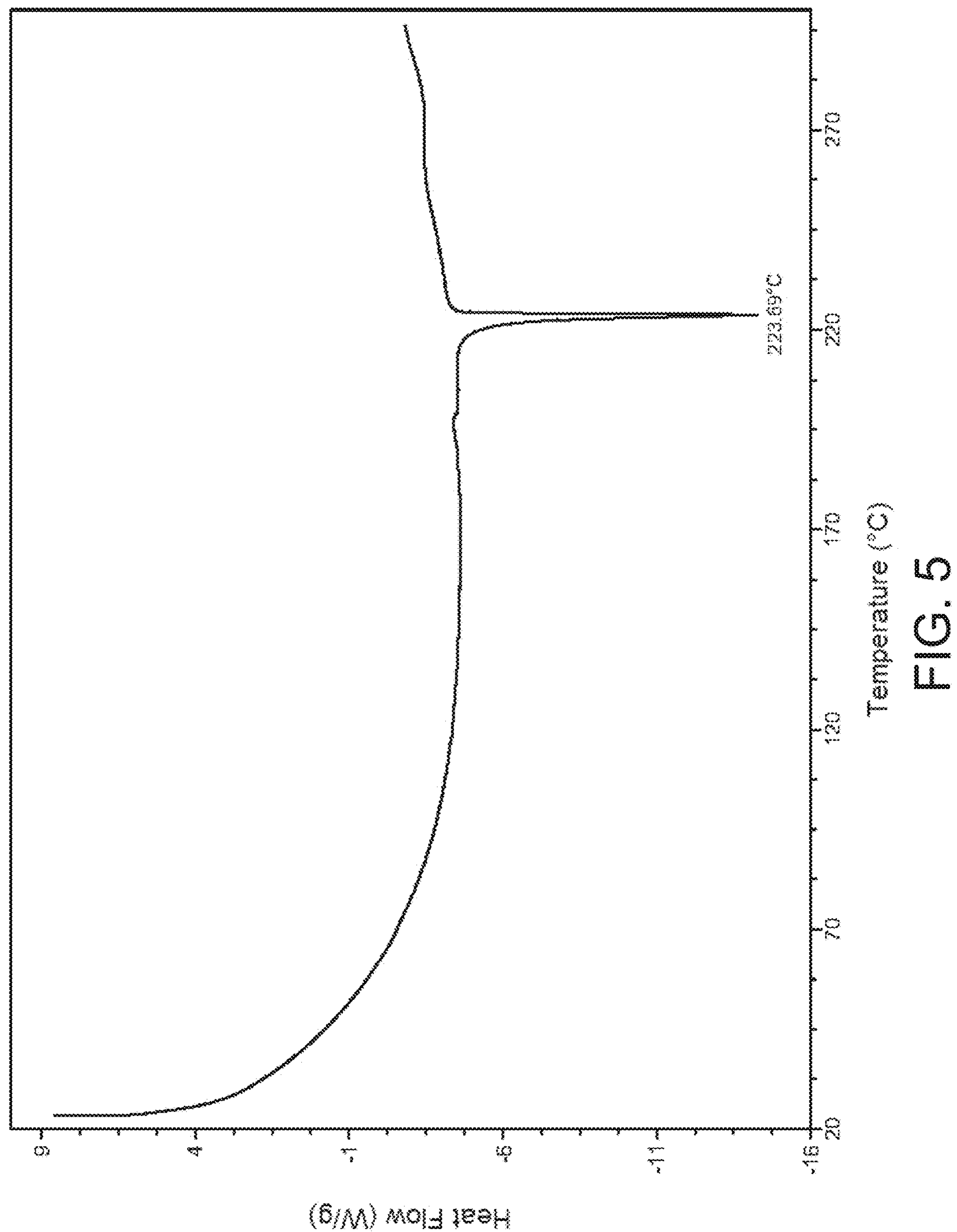
FIG. 5 is a differential scanning calorimetry (DSC) pattern of the crystal form II of the compound of formula (I).
Figure 6:
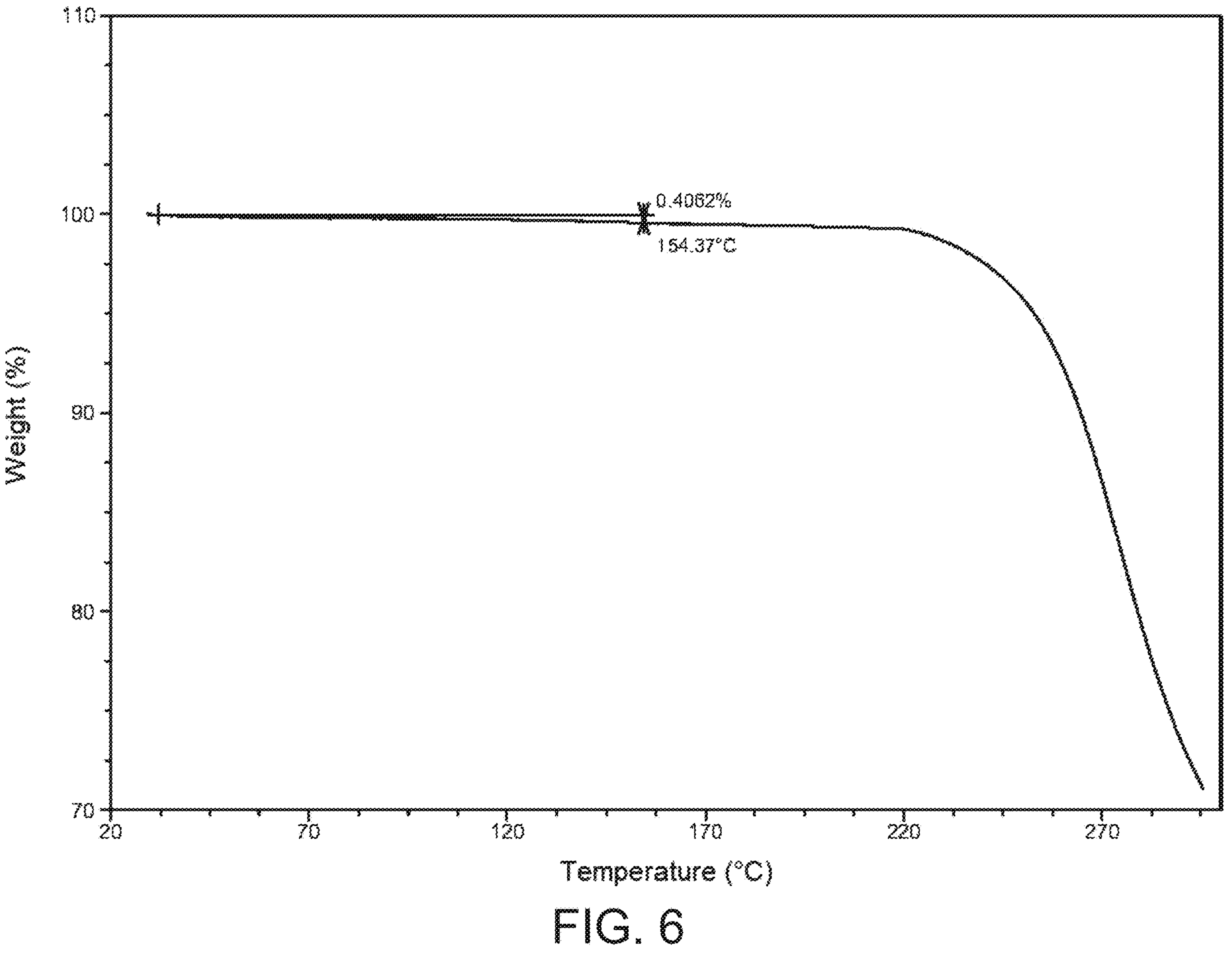
FIG. 6 is a thermogravimetric analysis (TGA) pattern of the crystal form II of the compound of formula (I).

7. The crystal form I of claim 1, wherein the crystal form I has a differential scanning calorimetry pattern substantially as shown in FIG. 2.

8. A pharmaceutical composition, comprising the crystal form I of claim 1, and pharmaceutically acceptable carriers, excipients, diluents, adjuvants or combinations thereof.

9. A method for treating or reducing hypoxia-inducible factor-related and/or erythropoietin-related diseases in a patient, comprising administering a pharmaceutically acceptable effective dose of the crystal form I of claim 1, wherein the disease is anemia, ischemia, vascular disease angina pectoris, myocardial ischemia. myocardial infarction, metabolic disorder, or wound healing.

10. A method for treating or reducing hypoxia-inducible factor-related and/or erythropoietin-related diseases in a patient, comprising administering a pharmaceutically acceptable effective dose of the pharmaceutical composition of claim 8, wherein the disease is anemia, ischemia, vascular disease, angina pectoris, myocardial ischemia, myocardial infarction, metabolic disorder, or wound healing.

* * * * *